United States Patent [19]
LaTorse et al.

[11] Patent Number: 5,514,719
[45] Date of Patent: May 7, 1996

[54] FUNGICIDAL PHENYLBENZAMIDES

[75] Inventors: Marie-Pascale LaTorse, Sourcieux les Mines; Christian Schmitz, Anse, both of France

[73] Assignee: Rhone-Poulenc Agrochimie, Lyon Cedex, France

[21] Appl. No.: 261,706

[22] Filed: Jun. 17, 1994

Related U.S. Application Data

[63] Continuation of Ser. No. 84,167, Jun. 30, 1993, abandoned.

[30] Foreign Application Priority Data

Jun. 30, 1992 [FR] France ................. 92 08290

[51] Int. Cl.$^6$ .................. A01N 37/18; C07C 233/65
[52] U.S. Cl. .................................. 514/622; 564/171
[58] Field of Search .......................... 564/171; 514/622

[56] References Cited

U.S. PATENT DOCUMENTS

| | | | |
|---|---|---|---|
| 4,921,870 | 5/1990 | Kramer et al. | 514/383 |
| 4,960,456 | 10/1990 | Holmwood et al. | 71/92 |
| 5,342,835 | 8/1994 | Pepin et al. | 514/227.5 |

FOREIGN PATENT DOCUMENTS 0360701  3/1990  European Pat. Off. .

*Primary Examiner*—Brian M. Burn
*Attorney, Agent, or Firm*—Burns, Doane, Swecker & Mathis

[57] ABSTRACT

The invention provides agriculturally useful fungicidal phenylbenzamides of the formula

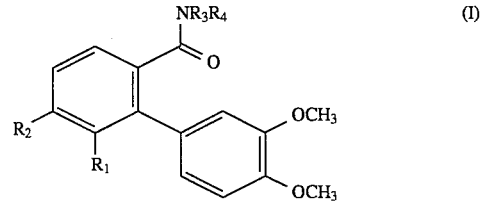

wherein $R_1$ and $R_2$, which are identical or different, are each a hydrogen or halogen atom or an optionally halogenated alkyl radical having from 1 to 6 carbon atoms; and $R_3$ and $R_4$, which are identical or different, are each an alkyl radical having from 1 to 4 carbon atoms, or $R_3$ and $R_4$, taken together with the nitrogen atom to which they are attached, form a morpholino radical.

12 Claims, No Drawings

FUNGICIDAL PHENYLBENZAMIDES

This application is a continuation of application Ser. No. 08/084,167, filed Jun. 30, 1993, (now abandoned).

The present invention relates to new phenylbenzamide derivatives, their preparation, fungicidal compositions containing them and their use in protecting plants against fungal diseases.

European Application No. 0,360,701 describes a very great number of amide derivatives and especially phenylbenzamides, as well as their use as active materials for controlling fungal diseases of plants. The examples show in particular their preventive activity against diseases such as mildews.

Applicants have now discovered that a narrow selection of these derivatives have the properties already described but furthermore, and surprisingly, such an activity at an excellent level as well as a notable curative activity.

More precisely, the present invention relates to phenylbenzamide derivatives of the formula:

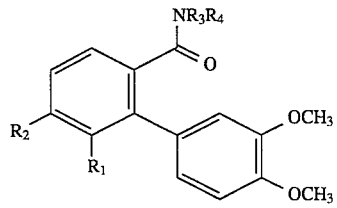

wherein $R_1$ and $R_2$, which are identical or different, are each a hydrogen or halogen atom or an optionally halogenated alkyl radical having from 1 to 6 carbon atoms; and $R_3$ and $R_4$, which are identical or different, are each an alkyl radical having from 1 to 4 carbon atoms, or $R_3$ and $R_4$ taken together with the nitrogen atom to which they are attached form a morpholino radical.

The optionally halogenated alkyl radical represented by $R_1$ and/or $R_2$ preferably has from 1 to 4 carbon atoms.

A preferred group of compounds encompassed by formula (I) are the compounds in which $R_1$ and $R_2$, which are identical or different, are each a hydrogen or chlorine atom or a trifluoromethyl radical.

Particularly preferred compounds encompassed by formula (I) are the compounds in which one of $R_1$ and $R_2$ is a hydrogen atom and the other of $R_1$ and $R_2$ is a trifluoromethyl radical; and the compounds in which $R_1$ and $R_2$ are each a chlorine atom.

Another preferred group of compounds encompassed by formula (I) are the compounds in which $R_3$ and $R_4$, which are identical or different, are each a methyl or ethyl radical.

Yet another preferred group of compounds encompassed by formula (I) are the compounds in which $R_3$ and $R_4$, taken together with the nitrogen atom to which they are attached, form a morpholino radical.

Especially preferred compounds of the invention are the following:

(1) N,N-Diethyl-2-(3,4-dimethoxyphenyl)-4-(trifluoromethyl)benzamide;
(2) 2-(3,4-dimethoxyphenyl)-4-trifluoromethyl-1-morpholinocarbonylbenzene;
(3) N-Ethyl-N-methyl-2-(3,4-dimethoxyphenyl)-4-(trifluoromethyl)benzamide;
(4) N-Ethyl-N-methyl-2-(3,4-dimethoxyphenyl)-3,4-dichlorobenzamide; and
(5) N,N-Diethyl-2-(3,4-dimethoxyphenyl)-3,4-dichlorobenzamide.

The compounds of formula (I) can be prepared according to the process described in the aforementioned European Application No. 0,360,701, or according to one of the two other processes described below.

According to a first process, the compounds of formula (I) above can be prepared from the corresponding compounds of the formula

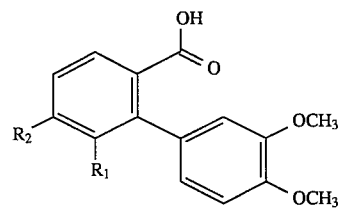

after activation of the acidic functional group by treating said formula (II) compounds with a suitable activating agent [preferably thionyl chloride ($SOCl_2$), phosphoryl chloride ($POCl_3$), phosphorus trichloride or pentachloride ($PCl_3$, $PCl_5$), dicyclohexylcarbodiimide, carbonyldiimidazole, a lower alkyl chloroformate (e.g. methyl chloroformate), trifluoroacetic anhydride or the like] and then reacting the resultant intermediate with an amine of the formula $HNR_3R_4$ in the presence of an organic or inorganic base in an organic solvent (preferably a chlorinated or aromatic solvent or an ether such as THF).

The compounds of formula (II) above can be prepared by saponifying the corresponding compounds of the formula

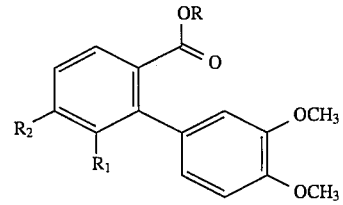

wherein R is an aliphatic radical, preferably an alkyl radical having 1 to 4 carbon atoms. The reaction is carried out in an aliphatic alcohol such as ethanol in the presence of water and an inorganic base derived from an alkali metal (preferably an alkali metal hydroxide such as potassium hydroxide or sodium hydroxide), at a temperature from about room temperature to the reflux temperature of the reaction mixture. The reaction mixture is then treated with an organic or inorganic acid, such as, preferably, hydrochloric acid, to afford the corresponding compound of formula (II).

The compounds of formula (III) can be prepared by an aryl coupling reaction between the compounds of the formula

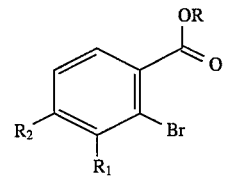

and 3,4-dimethoxyphenylboronic acid in the presence of a catalyst [such as, for example, tetrakis(triphenyl-phosphine)palladium]. In order to provide good selectivity, it is understood that neither $R_1$ nor $R_2$ may be a bromine or iodine atom.

3,4-Dimethoxyphenylboronic acid can be prepared by analogy to methods described in the literature, for example *Organic Synthesis, Coll.* Vol. 4, page 68 or *Journal of Organic Chemistry*, 49, pp. 5237–5243.

The esters of formula (IV) can be prepared by esterifying the corresponding acids of the formula

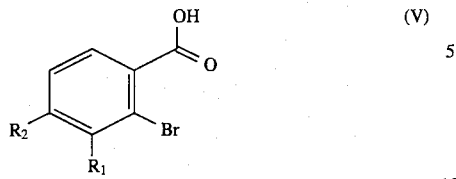 (V)

by reaction with an aliphatic alcohol ROH wherein R is preferably an alkyl radical having 1 to 4 carbon atoms, such as methanol or ethanol, in the presence of a suitable amount (typically from 1 to 20%) of an inorganic acid, such as gaseous hydrochloric acid or concentrated sulfuric acid, generally at the reflux temperature of the reaction mixture. The product can be isolated by precipitation in water or extraction using an organic solvent.

The acids of formula (V) can be prepared by diazotization of the corresponding anthranilic acids of the formula

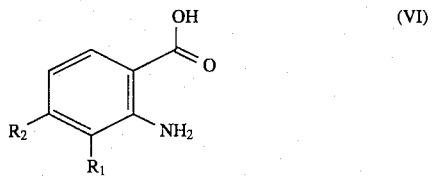 (VI)

according to known methods.

The preparation of the anthranilic acids of formula (VI) is amply described in the literature.

In a second process, the compounds of formula (I) can be prepared from the corresponding compounds of the formula

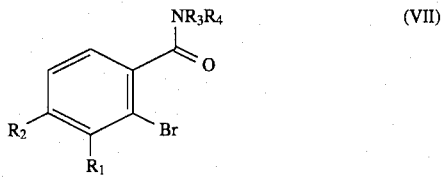 (VII)

by coupling with 3,4-dimethoxyphenylboronic acid, analogously in all respects to the process described above for the preparation of the compounds of formula (III) from the corresponding compounds of formula (IV).

The compounds of formula (VII) can be prepared from the corresponding compounds of the formula

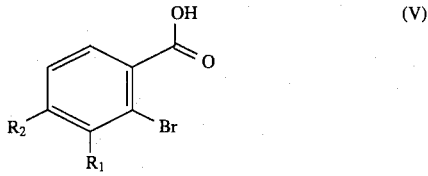 (V)

by a process analogous in all respects to the process described above for the preparation of the compounds of formula (I) from the corresponding compounds of formula (II).

In order to further illustrate the present invention and the advantages thereof, the following specific examples are given, it being understood that same are intended as illustrative and in nowise limitative.

EXAMPLE 1

N,N-Diethyl-2-(3,4-dimethoxyphenyl)-4-(trifluoromethyl)benzamide (Compound No. 1) (Formula I with $R_1$=H, $R_2$=$CF_3$, $R_3$=$R_4$=$C_2H_5$).

500 ml of 1,2-dichloroethane, 60 g (0.184 mol) of 2-(3,4-dimethoxyphenyl)-4-(trifluoromethyl)benzoic acid and 5 ml of N,N-dimethylformamide are introduced successively into a 1000 ml round-bottomed flask. 20 ml of thionyl chloride (0.276 mol) are then run in dropwise with stirring and while cooling at 0° C. When the addition is finished, the reaction mixture is heated progressively to 55° C. over 2 hours and then evaporated to dryness. The residue is taken up in 200 ml of tetrahydrofuran and then poured dropwise into a solution containing 58 ml (0.55 mol) of diethylamine in 200 ml of tetrahydrofuran maintained at a temperature below 10° C. When the addition is finished, the reaction mixture is stirred at room temperature for one hour and then evaporated to dryness. The residue is taken up in dichloromethane and washed successively with 1N HCl and distilled water. After drying over magnesium sulfate, the organic phase is evaporated under reduced pressure to provide 62.3 g (yield: 89%) of N,N-diethyl-2-(3,4-dimethoxyphenyl)-4-(trifluoromethyl)benzamide in the form of a white solid melting at 109°–110° C.

The two compounds below were prepared analogously:

2-(3,4-dimethoxyphenyl)-4-trifluoromethyl-1-morpholinocarbonylbenzene: 60 g (82.5%) melting at 130° C. (Compound No. 2) (Formula I with $R_1$=H, $R_2$=$CF_3$, $R_3$+$R_4$=morpholino).

N-ethyl-N-methyl-2-(3,4-dimethoxyphenyl)-4-(trifluoromethyl)benzamide: 71.2 g (81%) melting at 103°–104° C. (Compound No. 3) (Formula I with $R_1$=H, $R_2$=$CF_3$, $R_3$=$CH_3$, $R_4$=$C_2H_5$).

EXAMPLE 2

2-(3,4-Dimethoxyphenyl)-4-(trifluoromethyl)benzoic acid (Formula II with $R_1$=H, $R_2$=$CF_3$).

1000 ml of absolute ethanol, 290 g (0.82 mol) of ethyl 2-(3,4-dimethoxyphenyl)-4-(trifluoromethyl)benzoate and 170 ml (0.164 mol) of 10N sodium hydroxide solution are introduced successively into a 2-liter round-bottomed flask. The reaction mixture is brought to reflux for two hours and then evaporated to dryness under reduced pressure. The residue is taken up in 2.5 liters of water and extracted successively with 500 ml of ethyl acetate and 500 ml of pentane. 500 g of crushed ice are added to the aqueous phase which is then treated with an excess of concentrated hydrochloric acid. The precipitate which forms is filtered on sintered glass and then dried under a stream of air; there is thus obtained 240.5 g (yield: 90%) of 2-(3,4-dimethoxyphenyl)-4-(trifluoromethyl)benzoic acid in the form of a light-beige solid melting at 194° C.

EXAMPLE 3

Ethyl 2-(3,4-dimethoxyphenyl)-4-(trifluoromethyl)benzoate (Formula III with $R_1$=H, $R_2$=$CF_3$, R=$C_2H_5$).

263 g (0.885 mol) of ethyl 2-bromo-4-(trifluoromethyl)benzoate, 750 ml of 1,2-dimethoxyethane, 4 g of tetrakis(triphenylphosphine)palladium, 177 g (0.974 mol) of 3,4-dimethoxyphenylboronic acid and 1000 ml of a 2M aqueous sodium carbonate solution are introduced successively, under an inert atmosphere, into a four-liter round-bottomed flask. The reaction mixture is brought to reflux for fourteen hours and then evaporated to a third under reduced pressure. The reaction mixture is poured onto two liters of water; the precipitate which forms is filtered on sintered glass, rinsed with water and then dried under a stream of air. There is thus obtained 294 g (yield: 94%) of ethyl 2-(3,4-dimethoxyphenyl)-4-(trifluoromethyl)benzoate in the form of a beige solid melting at 89° C.

EXAMPLE 4

Ethyl 2-bromo-4-(trifluoromethyl)benzoate (Formula IV with $R_1$=H, $R_2$=$CF_3$, R=$C_2H_5$).

238 g (0.885 mol) of 2-bromo-4-(trifluoromethyl)benzoic acid, 1000 ml of absolute ethanol and 100 ml of concentrated sulfuric acid are introduced successively into a 2-liter round-bottomed flask. The reaction mixture is brought to reflux for 6 hours and then poured, after cooling, onto 2.5 liters of ice-cold water; the oil formed is extracted with ethyl acetate. The organic phase is successively washed with water, with 1N sodium hydroxide solution and then again with water. After drying over magnesium sulfate, the solvent is evaporated to provide 263 g (yield: 100%) of ethyl 2-bromo-4-(trifluoromethyl)benzoate in the form of a yellow oil.

EXAMPLE 5

2-Bromo-4-(trifluoromethyl)benzoic acid (Formula V with $R_1$=H, $R_2$=$CF_3$).

205 g (1 mol) of 4-(trifluoromethyl)anthranilic acid, 600 ml of glacial acetic acid and 400 ml of 47% hydrobromic acid are introduced successively into a three-liter round-bottomed flask. After dissolution, the reaction mixture is cooled to −10° C., diluted with 400 ml of water and then treated dropwise with a solution of 69 g (1 mol) of sodium nitrite in 200 ml of water while maintaining the temperature below 0° C. When the addition is finished, the reaction mixture is stirred at 0° C. for 2 hours. This solution is run in dropwise into a six-liter reactor containing 143.5 g (1 mol) of cuprous bromide in 500 ml of 47% hydrobromic acid maintained at 60° C. When the addition is finished, the reaction mixture is stirred at 60° C. for one hour, cooled to room temperature and then poured into two liters of ice-cold water. The precipitate which forms is filtered on sintered glass, washed with water and then dried under a stream of air. There is thus obtained 216 g (yield: 80%) of 2-bromo-4-(trifluoromethyl)benzoic acid in the form of a solid melting at 118.5° C.

The preparation of 4-(trifluoromethyl)anthranilic acid (Formula VI with $R_1$=H, $R_2$=$CF_3$) used in Example 5 is described in the literature.

EXAMPLE 6

Second process:

N-ethyl-N-methyl- 2-(3,4-dimethoxyphenyl)-3,4-dichlorobenzamide (Compound No. 4) (Formula I with $R_1$=$R_2$=Cl, $R_3$=$CH_3$, $R_4$=$C_2H_5$).

12.4 g (0.040 mol) of N-ethyl-N-methyl-2-bromo- 3,4-dichlorobenzamide, 100 ml of 1,2-dimethoxyethane, 0.5 g of tetrakis(triphenylphosphine)palladium, 8 g (0.044 mol) of 3,4-dimethoxyphenylboronic acid and 60 ml of a 2M aqueous sodium carbonate solution are introduced successively, under an inert atmosphere into a 500 ml round-bottomed flask. The reaction mixture is brought to reflux for fourteen hours and then evaporated to a third under reduced pressure. The reaction mixture is poured onto two liters of water; the precipitate which forms is filtered on sintered glass, rinsed with water and then dried under a stream of air. After purification by chromatography, there is thus obtained 10.3 g (yield: 70%) of N-ethyl-N-methyl- 2-(3,4-dimethoxyphenyl)-3,4-dichlorobenzamide in the form of a white solid melting at 102° C.

The following compound was prepared analogously:

N,N-diethyl-2-(3,4-dimethoxyphenyl)-3,4-dichlorobenzamide: 6.5 g (47.8%) melting at 108° C. (Compound No. 5) (Formula I with $R_1$=$R_2$=Cl, $R_3$=$R_4$= $C_2H_5$).

EXAMPLE 7

N-Ethyl-N-methyl-2-bromo-3,4-dichlorobenzamide (Formula VII with $R_1$=$R_2$=Cl, $R_3$= $CH_3$, $R_4$=$C_2H_5$).

200 ml of 1,2-dichloroethane, 14 g (0.052 mol) of 2-bromo-3,4-dichlorobenzoic acid and 2 ml of N,N-dimethylformamide are introduced successively into a 500 ml round-bottomed flask. 11.5 ml of thionyl chloride (0.078 mol) are then run in dropwise with stirring and while cooling at 0° C. When the addition is finished, the reaction mixture is heated progressively to 55° C. over 2 hours and then evaporated to dryness. The residue is taken up in 50 ml of tetrahydrofuran and then poured dropwise into a solution containing 13 ml (0.15 mol) of N-methylethylamine in 50 ml of tetrahydrofuran maintained at a temperature below 10° C. When the addition is finished, the reaction mixture is stirred at room temperature for one hour and then evaporated to dryness. The residue is taken up in dichloromethane and washed successively with 1N HCl and distilled water. After drying over magnesium sulfate, the organic phase is evaporated under reduced pressure to provide 12.4 g (yield: 80%) of N-ethyl-N-methyl-2-bromo- 3,4-dichlorobenzamide in the form of a white solid melting at 71° C.

The following compound was prepared analogously:

N,N-diethyl-2-bromo-3,4-dichlorobenzamide (Formula VII with $R_1$=$R_2$=Cl, $R_3$=$R_4$=$C_2H_5$): 13.6 g (yield: 83.7%).

The preparation of 2-bromo-3,4-dichlorobenzoic acid (Formula V with $R_1$=$R_2$=Cl) used in Example 7 was carried out as above in Example 5: the product was obtained in the form of a beige powder, 63 g (yield: 81%), melting at 196° C.

EXAMPLE 8

In vivo curative test under glass on grape downy mildew (*Plasmopara viticola*):

Vine cuttings (*Vitis vinifera*), of Chardonnay variety, are grown in pots. When these seedlings are 2 months old (8 to 10-leaf stage, height of 20 to 30 cm), they are infected, by spraying, with an aqueous suspension of spores of *Plasmopara viticola*, responsible for grape downy mildew, at a concentration of approximately 5 ml/seedling (or approximately 1×10$^5$ spores per seedling).

After this infection, the vine seedlings are incubated for two days at approximately 18° C. in an atmosphere saturated with moisture and then for five days at approximately 20°–22° C. under 90–100% relative humidity.

The infected plants are then treated, by spraying, with an aqueous suspension or solution of the material to be tested, at the desired concentration and containing a condensate of 20 molecules of ethylene oxide with sorbitan monooleate to a limit of half the active material concentration. Each vine seedling receives approximately 5 ml of the solution or dispersion. The treatment is carried out on two seedlings for each concentration of active material to be tested. Contaminated seedlings, used as controls, are treated with a solution which does not contain active material but which contains the same condensate of ethylene oxide with sorbitan monooleate at an identical concentration.

After drying for 24 hours, the results obtained in the case of the seedlings treated with the active material to be tested are compared with those obtained in the case of the seedlings used as controls.

Under these conditions, it is observed that, at a dose of 110 ppm (0.11 g/l), Compounds 1 to 5 led to at least 95% inhibition in the development of the fungus, i.e. an activity equivalent to that of the commercial reference cymoxanil, taken under the same conditions.

These examples illustrate well the fungicidal properties of the compounds according to the invention.

The latter may, in effect, be used as fungicidal active materials, in particular for controlling fungal diseases of plants, especially those due to pathogenic fungi, especially those of the Oomycetes family of the Phytophthora sp type, for example *Phytophthora infestans* (potato or tomato late blight), *Phytophthora citrophthora, Phytophthora capsici, Phytophthora cactorum, Phytophthora palmivora, Phytophthora cinnamoni, Phytophthora megasperma*, or *Phytophthora parasitica*, Peronospora sp type (especially tobacco downy mildew), Plasmopara sp type, especially *Plasmopara viticola* (grape downy mildew) and *Plasmopara halstedei* (sunflower downy mildew), Pseudoperonospora sp type (especially downy mildew of the Cucurbitaceae and hop downy mildew), or *Bremia lactucae* type (lettuce downy mildew), as well as soil fungi.

They are advantageously applied at doses of 0.01 to 5 kg/ha, and more specifically of approximately 0.02 to 2 kg/ha.

For their practical use, the compounds according to the invention are rarely used on their own. Most often they form part of compositions. These compositions, which can be used for protecting plants against fungal diseases or in plant growth regulatory compositions, contain, as active material, at least one compound according to the invention as described above in combination with solid or liquid inert vehicles which are acceptable in agriculture, and/or surface-active agents which are compatible with the active material and which are also acceptable in agriculture. In particular, the customary inert vehicles and the customary surface-active agents can be used.

The term "vehicle", in the present account, means a natural or synthetic, organic or inorganic material with which the active material is combined in order to facilitate its application to the plant, to seeds or to the soil. This vehicle is therefore generally inert and it has to be acceptable in agriculture, especially to the treated plant. The vehicle can be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons) or gaseous.

The surface-active agent can be an emulsifying, dispersing or wetting agent of ionic or nonionic type. There may be cited, for example, salts of poly(acrylic acids), salts of lignosulfonic acids, salts of phenolsulfonic or naphthalenesulfonic acids, polycondensates of ethylene oxide with fatty alcohols or fatty acids or fatty amines, substituted phenols (especially alkylphenols or arylphenols), salts of esters of sulfosuccinic acids, derivatives of taurine (especially alkyltaurates) and phosphoric esters of polycondensates of ethylene oxide with alcohols or phenols. The presence of at least one surface-active agent is generally indispensable where the active material and/or the inert vehicle are not soluble in water and where the vector agent of the application is water.

The compositions used in the invention can be in fairly diverse, fluid, liquid or solid forms.

As fluid composition forms, or liquids, there may be mentioned especially emulsifiable concentrates, emulsions, aqueous suspension concentrates, pastes, solutions, in particular water-soluble concentrates, concentrated solutions in an organic medium (ULV solution), and aerosols.

The emulsifiable or soluble concentrates most often comprise 10 to 80% of active material, while the ready-to-apply solutions or emulsions contain, for their part, 0.001 to 20% of active material. In addition to the active material and the solvent, the emulsifiable concentrates can contain, when this is necessary, a suitable co-solvent and 2 to 20% of suitable additives such as stabilizing agents, penetration agents, corrosion inhibitors, dyes or adhesives.

It is possible, by diluting these concentrates with water, to obtain emulsions of any desired concentration which are particularly suitable for application to crops.

By way of examples, the composition of several emulsifiable concentrates will now be given:

| EC Example 1: | |
| --- | --- |
| active material (Compound No. 1) | 250 g/l |
| epoxidized vegetable oil | 25 g/l |
| mixture of alkylarylsulfonate and of ether of polyglycol and fatty alcohols | 100 g/l |
| dimethylformamide | 50 g/l |
| xylene | 575 g/l |
| EC Example 2: | |
| active material (Compound No. 2) | 400 g/l |
| alkaline dodecylbenzenesulfonate | 24 g/l |
| condensate of 10 molecules of ethylene oxide with nonylphenol | 16 g/l |
| cyclohexanone | 200 g/l |
| aromatic solvent | qs for 1 liter |

It is possible, by diluting these concentrates with water, to obtain emulsions of any desired concentration which are particularly suitable for application to leaves.

The suspension concentrates, which can also be applied by spraying, are prepared so as to produce a stable fluid product which does not settle out and they generally contain from 10 to 75% of active material, from 0.5 to 15% of surface-active agents, from 0.1 to , 10% of thixotropic agents, from 0 to 10% of suitable additives, such as antifoaming agents, corrosion inhibitors, stabilizing agents, penetration agents and adhesives and, as vehicle, water or an organic liquid in which the active material has little or no solubility: certain solid organic materials or inorganic salts can be dissolved in the vehicle to help in preventing sedimentation or as antifreeze for the water.

By way of example, the composition of a number of aqueous suspension concentrates will now be given:

| ASC Example 1: | |
| --- | --- |
| An aqueous suspension is prepared comprising: | |
| active material (Compound No. 3) | 100 g/l |
| wetting agent (polycondensate of ethylene oxide with alkylphenol) | 5 g/l |
| dispersing agent (Na naphthalene sulfonate) | 10 g/l |
| antifreeze (propylene glycol) | 100 g/l |
| thickening agent (polysaccharide) | 3 g/l |
| biocide (formaldehyde) | 1 g/l |
| water | q.s. for 1 liter |
| ASC Example 2: | |
| An aqueous suspension is prepared comprising: | |
| active material (Compound No. 4) | 250 g/l |
| wetting agent (polycondensate of ethylene oxide with a C13 synthetic | 10 g/l |

| | |
|---|---|
| alcohol) | |
| dispersing agent (sodium lignosulfonate) | 15 g/l |
| antifreeze (urea) | 50 g/l |
| thickening agent (polysaccharide) | 2.5 g/l |
| biocide (formaldehyde) | 1 g/l |
| water | q.s. for 1 liter |

ASC Example 3:

| | |
|---|---|
| An aqueous suspension is prepared comprising: | |
| active material (Compound No. 5) | 500 g/l |
| wetting agent (polycondensate of ethylene oxide with a C13 synthetic alcohol) | 10 g/l |
| dispersing agent (salified phosphate of a condensate of ethylene oxide with polyarylphenol) | 50 g/l |
| antifreeze (propylene glycol) | 100 g/l |
| thickening agent (polysaccharide) | 1.6 g/l |
| biocide (sodium salt of methyl 4-hydroxybenzoate) | 3.3 g/l |
| water | q.s. for 1 liter |

There may be mentioned, as solid composition forms, powders for dusting (containing the active materials at a content of up to 100%) and granules, especially those obtained by extrusion, by compacting, by impregnation of a granulated vehicle, or by granulation from a powder (the content of the compound of formula (I) in these granules being between 0.5 and 80% for the latter cases).

The wettable powders (or sprayable powders) are generally prepared so that they contain 10 to 95% of active material, and they generally contain, in addition to the solid vehicle, from 0 to 5% of a wetting agent, from 3 to 10% of a dispersing agent and, when necessary, from 0 to 10% of one or more stabilizing agents and/or other additives, such as penetration agents, adhesives, or anti-caking agents, dyes, and the like.

By way of example, the composition by weight of a number of wettable powders will now be given:

| WP Example 1: | |
|---|---|
| active material (Compound No. 1) | 10% |
| condensate of 8 to 10 mol of ethylene oxide with C13 branched-type synthetic oxo alcohol (wetting agent) | 0.75% |
| neutral calcium lignosulfonate (dispersing agent) | 12% |
| calcium carbonate (inert filler) | qs for 100% |

| WP Example 2: | |
|---|---|
| active material (Compound No. 2) | 50% |
| condensate of ethylene oxide with fatty alcohol (wetting agent) | 2.5% |
| condensate of ethylene oxide with styrylphenol (dispersing agent) | 5% |
| chalk (inert vehicle) | 42.5% |

WP Example 3

The same ingredients are used as in the above example, in the proportions below:

| | |
|---|---|
| active material (Compound No. 2) | 75% |
| wetting agent | 1.5% |
| dispersing agent | 8% |
| calcium carbonate (inert filler) | qs for 100% |

| WP Example 4: | |
|---|---|
| active material (Compound No. 3) | 90% |
| condensate of ethylene oxide with fatty alcohol (wetting agent) | 4% |
| condensate of ethylene oxide with styrylphenol (dispersing agent) | 6% |

In order to obtain these sprayable powders or wettable powders, the active material is intimately mixed in suitable mixers with the additional substances and the mixture is milled in mills or other suitable grinders. Sprayable powders are thereby obtained whose wettability and suspensibility are advantageous; they can be suspended in water at any desired concentration, and this suspension can be used very advantageously in particular for application to plant leaves.

The compounds of formula (I) can also be used in the form of powders for dusting; it is also possible to use a composition comprising 50 g of active material and 950 g of talc; it is also possible to use a composition comprising 20 g of active material, 10 g of finely divided silica and 970 g of talc; these constituents are mixed and milled and the mixture is applied by dusting.

The granules for dusting have sizes between 0.1 and 2 mm and can be manufactured by agglomeration or impregnation. In general, the granules contain 0.5 to 25% of active material and 0 to 10% of additives such as stabilizing agents, slow-release modifying agents, binders and solvents.

Two examples of granule compositions will now be given:

| G Examples 1 and 2: | | |
|---|---|---|
| active material (Compound No. 4) | 50 g | 200 g |
| propylene glycol | 50 g | 50 g |
| cetyl polyglycol ether | 2.5 g | 2.5 g |
| polyethylene glycol | 35 g | 35 g |
| kaolin (particle size: 0.3 to 0.8 mm) | 910 g | 760 g |

The compounds according to the invention may advantageously be formulated in the form of water-dispersible granules also included in the scope of the invention.

These dispersible granules, with an apparent density generally of between approximately 0.3 and 0.6, have a particle size generally between approximately 150 and 2000, and preferably between 300 and 1500 microns.

The active material content of these granules is generally between approximately 1% and 90%, and preferably between 25% and 90%.

The remainder of the granule is essentially composed of a solid filler and optionally of surface-active adjuvants which confer water-dispersibility properties on the granule. These granules can be essentially of two distinct types depending upon whether the filler used is water-soluble; it can be inorganic and, preferably, organic. Excellent results have been obtained with urea. In the case of an insoluble filler, the latter is preferably inorganic, such as, for example, kaolin or bentonite. It is then accompanied by surface-active agents (in an amount of 2 to 20% by weight of the granule), surface-active adjuvants of which more than half consists of at least one essentially anionic dispersing agent such as a poly(alkali metal or alkaline-earth metal naphthalene sulfonate) or alkali metal or alkaline-earth metal lignosulfonate, the remainder consisting of nonionic or anionic wetting agents such as an alkali metal or alkaline-earth metal alkylnaphthalene sulfonate.

Moreover, although this is not indispensable, it is possible to add other adjuvants such as antifoaming agents.

The granule according to the invention can be prepared by mixing the required ingredients and then granulating according to several techniques known per se (pelletizer, fluid bed, atomizer, extrusion, and the like). Generally, the preparation is completed by crushing followed by sieving to the particle size chosen within the abovementioned limits.

Preferably, it is obtained by extrusion. By carrying out the preparation as shown in the examples below, the following dispersible-granule compositions were prepared.

DG Example 1

90% by weight of active material (Compound No. 5) and 10% of urea in the pearl form are mixed in a mixer. The mixture is then milled in a pin mill. A damp powder is obtained which is extruded in a perforated-cylinder extruder. A granule is obtained which is dried and then crushed and sieved so as to retain only the granules with a size of between 150 and 2000 microns respectively.

DG Example 2

The following constituents are mixed in a mixer:

| | |
|---|---|
| active material (compound No. 2) | 75% |
| wetting agent (sodium alkylnaphthalene sulfonate) | 2% |
| dispersing agent (sodium polynaphthalene sulfonate) | 8% |
| water-insoluble inert filler (kaolin) | 15% |

DG Example 3:

| | |
|---|---|
| active material (Compound No. 1) | 20% |
| sodium alkylnaphthalene sulfonate | 2% |
| sodium methylenebis(naphthalene sulfonate) | 8% |
| kaolin | 70% |

This mixture is granulated in a fluid bed, in the presence of water, and is then dried, crushed and sieved so as to produce granules of between 0.16 and 0.40 mm in size.

These granules can be used alone or in solution or dispersion in water so as to produce the required dose. They can also be used to prepare combinations with other active materials, especially fungicides, the latter being in the form of wettable powders or of granules or aqueous suspensions.

The compounds according to the invention can also be formulated in the form of organic solutions which can be encapsulated, especially by interfacial polymerization, in capsules having polymeric walls, for example based on polyamides, polyureas or urea polyamides. These capsules are found in the form of a concentrated aqueous dispersion which can be diluted at the time of use to produce a spraying mixture.

As has already been said, the aqueous dispersions and emulsions, for example compositions obtained by diluting a wettable powder or an emulsifiable concentrate according to the invention using water, are included within the general scope of the compositions which can be used in the present invention. The emulsions can be of water-in-oil or oil-in-water type and they can have a thick consistency like that of a "mayonnaise".

The invention moreover relates to a process for the treatment, both curative and preventive, of plants against diseases caused by phytopathogenic fungi especially those of the Oomycetes family of the Phytophthora sp type, for example *Phytophthora infestans* (potato or tomato late blight), *Phytophthora citrophthora*, *Phytophthora capsici*, *Phytophthora cactorum*, *Phytophthora palmivora*, *Phytophthora cinnamoni*, *Phytophthora megasperma*, or *Phytophthora parasitica*, Peronospora sp type (especially tobacco downy mildew), Plasmopara sp type, especially *Plasmopara viticola* (grape downy mildew) and *Plasmopara halstedei* (sunflower downy mildew), Pseudoperonosora sp type (especially downy mildew of the Cucurbitaceae and hop downy mildew), or *Bremia lactucae* type (lettuce downy mildew), as well as soil fungi, this process being characterized in that a derivative according to the invention is applied. The excellent curative activity of the compounds according to the invention is particularly advantageous since it makes it possible to reduce the number of systemic preventive treatments while providing good control of parasites.

These derivatives can be used as the sole active material or in combination with another agrochemically active material, especially a fungicide such as, for example, those of the thiocarbamate or ethylenebis(dithiocarbamate) family, such as thiram, maneb, zineb and mancozeb, the phthalimide family, such as captan, captafol and folpet, the acylalanine family, such as metalaxyl, oxadixyl and benalaxyl, the family of copper-based compounds, the family of phosphonic acid derivatives such as fosetyl-aluminum, dithianon, chlorothalonil, cymoxanil, the thiadiazole family or the N,N'-dialkyl-N-phenylsufamide family.

This process is characterized in that it comprises applying to plants or to the locus in which they grow an effective quantity of a compound of formula (I), especially by applying an anti-fungal composition containing, as active material, an effective quantity of a compound according to the formula (I). "Effective quantity" is understood to mean a quantity sufficient to make possible control or destruction of the fungi present on these plants, in a curative as well as in a preventative sense, i.e. a fungicidally effective amount. The use doses can, however, vary within wide limits depending on the fungus to be combated, the type of crop, the climatic conditions and depending on the compound used.

In practice, doses ranging from 1 g/hl to 500 g/hl, corresponding substantially to doses of active material per hectare of approximately 10 g/ha to 5000 g/ha, generally give good results.

There may be mentioned, as examples of treatment processes which can be used, leaf or soil spraying, dusting, soaking, incorporation into the soil of granules, powders or mixtures, sprinkling, injection into trees, painting and seed treatment.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A compound of the formula

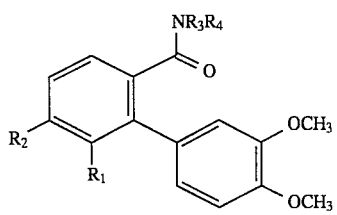

wherein $R_1$ is a hydrogen atom; $R_2$ is a trifluoromethyl radical; and $R_3$ and $R_4$, which are identical or different, are each an alkyl radical having from 1 to 4 carbon atoms.

2. The compound as claimed in claim 1, wherein $R_3$ and $R_4$, which are identical or different, are each a methyl or ethyl radical.

3. The compound as claimed in claim 2, which is:

N,N-diethyl-2-(3,4-dimethoxyphenyl)-4-(trifluoromethyl)benzamide; or

N-ethyl-N-methyl-2-(3,4-dimethoxyphenyl)-4-(trifluoromethyl)benzamide.

4. A fungicidal composition comprising a fungicidally effective amount of a compound of formula (I) as claimed in claim 1 and at least one member of the group consisting of agriculturally acceptable inert vehicles and agriculturally acceptable surface-active agents.

5. The composition as claimed in claim 4 wherein, in the compound of formula (I), $R_3$ and $R_4$, which are identical or different, are each a methyl or ethyl radical.

6. The composition as claimed in claim 5, wherein the compound of formula (I) is:

N,N-diethyl-2-(3,4-dimethoxyphenyl)-4-(trifluoromethyl)benzamide; or

N-ethyl-N-methyl-2-(3,4-dimethoxyphenyl)-4-(trifluoromethyl)benzamide.

7. A method for protecting plants against fungal disease, said method comprising applying to said plants or to the locus in which they grow a fungicidally effective amount of a compound of formula (I) as claimed in claim 1.

8. The method as claimed in claim 7, carried out as a curative treatment in plants infected with fungal disease.

9. A method for protecting plants against fungal disease, said method comprising applying to said plants or to the locus in which they grow a fungicidally effective amount of a composition as claimed in claim 4.

10. A method for protecting plants against fungal disease, said method comprising applying to said plants or to the locus in which they grow a fungicidally effective amount of a fungicidal composition comprising a fungicidally effective amount of a compound of the formula

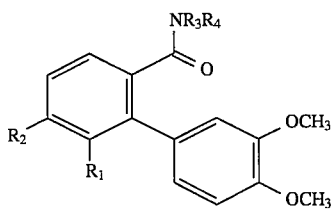

wherein $R_1$ is a hydrogen atom; $R_2$ is a trifluoromethyl radical; and $R_3$ and $R_4$, which are identical or different, are each an alkyl radical having from 1 to 4 carbon atoms; and at least one member of the group consisting of agriculturally acceptable inert vehicles and agriculturally acceptable surface-active agents; said method being carried out as a curative treatment in plants infected with fungal disease.

11. The method as claimed in claim 10 wherein, in the compound of formula (I), $R_3$ and $R_4$, which are identical or different, are each a methyl or ethyl radical.

12. The method as claimed in claim 11, wherein the compound of formula (I) is:

N,N-diethyl-2-(3,4-dimethoxyphenyl)-4-(trifluoromethyl)benzamide; or

N-ethyl-N-methyl-2-(3,4-dimethoxyphenyl)-4-(trifluoromethyl)benzamide.

* * * * *